United States Patent
Dickerson

(10) Patent No.: US 10,064,706 B2
(45) Date of Patent: Sep. 4, 2018

(54) ORTHODONTIC APPLIANCE

(71) Applicant: Todd Evan Dickerson, Phoenix, AZ (US)

(72) Inventor: Todd Evan Dickerson, Phoenix, AZ (US)

(*) Notice: Subject to any disclaimer, the term of this patent is extended or adjusted under 35 U.S.C. 154(b) by 0 days.

(21) Appl. No.: 15/845,003

(22) Filed: Dec. 18, 2017

(65) Prior Publication Data

US 2018/0104025 A1     Apr. 19, 2018

Related U.S. Application Data

(63) Continuation of application No. 15/398,991, filed on Jan. 5, 2017, now Pat. No. 9,848,960, which is a continuation of application No. 13/891,505, filed on May 10, 2013, now Pat. No. 9,539,066.

(51) Int. Cl.
| | |
|---|---|
| A61C 3/00 | (2006.01) |
| A61C 7/36 | (2006.01) |
| A61C 7/20 | (2006.01) |
| A61C 7/16 | (2006.01) |
| A61C 7/18 | (2006.01) |

(52) U.S. Cl.
CPC .......... *A61C 7/36* (2013.01); *A61C 7/16* (2013.01); *A61C 7/18* (2013.01); *A61C 7/20* (2013.01)

(58) Field of Classification Search
CPC .... A61C 7/36; A61C 7/16; A61C 7/18; A61C 7/20
USPC .......................................................... 433/19
See application file for complete search history.

(56) References Cited

U.S. PATENT DOCUMENTS

| | | |
|---|---|---|
| 757,809 A | 4/1904 | Houghton |
| 2,104,192 A | 1/1938 | Ford |
| 3,690,003 A | 9/1972 | Gerber |
| 4,373,914 A | 2/1983 | Colbert |
| 4,416,627 A | 11/1983 | Beazley |
| 4,462,800 A | 7/1984 | Jones |
| 4,496,317 A | 1/1985 | Hulsey |
| 4,867,679 A | 9/1989 | Rackley |
| 5,183,388 A | 2/1993 | Kumar |
| 5,240,413 A | 8/1993 | Ashinoff |
| 6,341,956 B1 | 1/2002 | Liou |
| 6,558,160 B2 | 5/2003 | Schnaitter et al. |
| 6,655,959 B2 | 12/2003 | Farzin-Nia et al. |
| 6,913,460 B2 | 7/2005 | Cleary et al. |
| 6,976,839 B2 | 12/2005 | Lluch |
| 7,018,202 B2 | 3/2006 | Teramoto |
| 7,238,022 B2 | 7/2007 | Lluch |
| 7,578,672 B2 | 8/2009 | Sheikh et al. |
| 7,618,257 B2 | 11/2009 | Lluch |
| 7,985,070 B2 | 7/2011 | Lluch |

(Continued)

*Primary Examiner* — Cris L Rodriguez
*Assistant Examiner* — Mirayda A Aponte
(74) *Attorney, Agent, or Firm* — Dorr, Carson & Birney PC

(57) ABSTRACT

An orthodontic appliance has a post attached to a first upper tooth, and a button with a recess attached to a second upper tooth. An elongated arm has an eye at one end through which the post is inserted to allow the elongated arm to rotate about the post, and a tip at the other end for removable insertion into the recess of the button. The length of the elongated arm is selectable to maintain a desired spacing between the first and second upper teeth (e.g., by cutting the tip of the elongated arm). An elastic extends from either the post or button to an attachment point on the patient's lower dental arch to exert a force between the patient's maxilla and mandible.

8 Claims, 3 Drawing Sheets

(56) References Cited

U.S. PATENT DOCUMENTS

2003/0170585 A1 9/2003 Wilkerson
2010/0285422 A1 11/2010 Wiechmann
2013/0089828 A1 4/2013 Borovinskih et al.

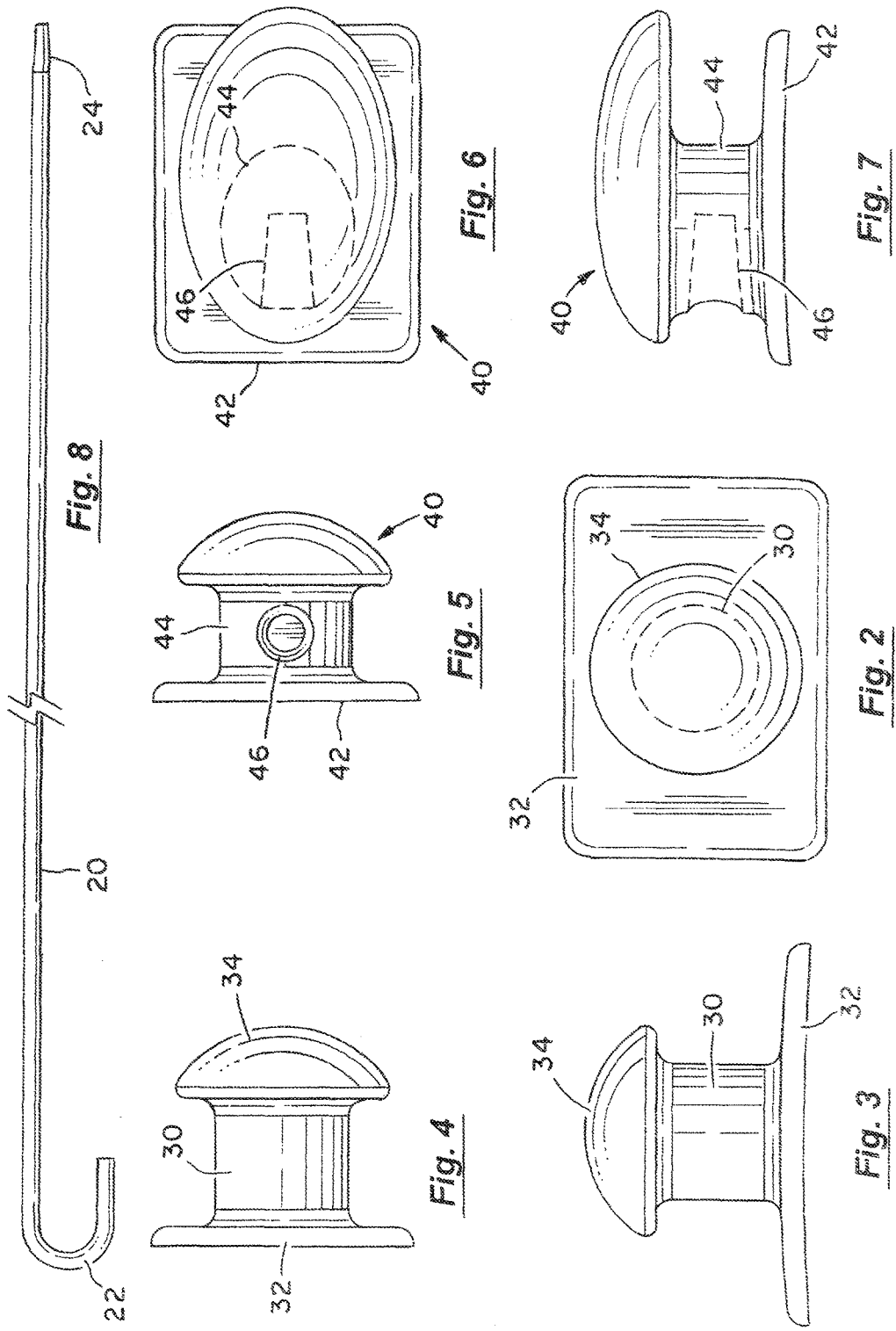

ORTHODONTIC APPLIANCE

RELATED APPLICATION

The present application is a continuation of the Applicant's co-pending U.S. patent application Ser. No. 15/398,991, entitled "Orthodontic Appliance," filed on Jan. 5, 2017, which is a continuation of U.S. patent application Ser. No. 13/891,505, filed on May 10, 2013, now U.S. Pat. No. 9,538,066, issued on Jan. 10, 2017.

BACKGROUND OF THE INVENTION

Field of the Invention

The present invention relates generally to the field of orthodontic appliances. More specifically, the present invention discloses a distalizing orthodontic appliance to maintain a desired position or occlusion between anterior and posterior teeth, primarily during class II correction.

Statement of the Problem

In orthodontics, a malocclusion refers to the misalignment of teeth, or an incorrect relation between the teeth of the upper and lower dental arches. With proper occlusion and a full complement of teeth, the mesiobuccal cusp of the upper first molar should align with the buccal groove of the lower first molar. The teeth should all fit on a line of occlusion. For the upper arch, the teeth should form a smooth curve through the central fossae of the posterior teeth and the cingulum of the anterior teeth. For the lower arch, the teeth should form a smooth curve through the buccal cusps of the posterior teeth and the incisal edges of the anterior teeth. Variations from these conditions result in three classes of malocclusion, as follows.

Class I malocclusion, or neutrocclusion, occurs when the relationship of the upper and lower first molars is normal, as discussed above, but the remaining teeth have problems in terms of their spacing, crowding, over- or under-eruption, etc.

Class II malocclusion is also known as distocclusion, retrognathism or overjet. The upper first molars do not rest in the buccal groove of the lower first molars, but rather are positioned anteriorly. The mesiobuccal cusp typically rests in between the lower first molars and the second premolars. This often results in an overbite or protrusion of the upper anterior teeth. In other words, the upper teeth are too far forward with respect to the lower teeth in class II malocclusion.

Class III malocclusion is also known as mesiocclusion, prognathism or negative overjet. The upper first molars are placed posteriorly to the mesiobuccal groove of the lower first molars. Therefore, the lower anterior teeth are more prominent than the upper anterior teeth. Class III malocclusion often occurs when the patient has a large mandible or a short maxillary bone.

In treatment of either class II or III malocclusion, many orthodontists seek to reposition the patient's mandible as a preliminary phase of orthodontic treatment before attaching conventional braces. In particular, the patient's mandible should be repositioned forward (or anteriorly) with respect to the maxilla for class II malocclusion. The mandible should be repositioned rearward (or posteriorly) for class III malocclusion.

A wide variety of orthodontic devices have been invented in the past to bias the mandible either anteriorly or posteriorly. However, a problem arises in that the forces exerted by an orthodontic appliance to bias the mandible toward a desired position must be carried in some manner by the patient's dental anatomy to the underlying skeletal structure. These relatively large forces can undesirably move the patient's teeth during this phase of treatment. Molars are relatively large and can withstand greater forces without movement, and therefore provide a convenient anchor point for some orthodontic appliances. In contrast, anterior teeth are smaller and more easily moved.

Nonetheless, a need exists to avoid undesired movement of teeth that can result from the forces involved in repositioning the patient's mandible. In particular, many orthodontic appliances for repositioning the mandible employ elastics, springs or other types of members extending diagonally from anterior teeth in one dental arch to posterior teeth in the other dental arch (e.g., from the upper cuspids to the lower molars). Devices of this type create a specific need to maintain proper spacing between a patient's anterior teeth and molars during the process of mandible repositioning.

One example of prior art in this field is known as the Carriere appliance, as shown in U.S. Pat. No. 6,976,839 (Lluch), U.S. Pat. No. 7,618,257 (Lluch), U.S. Pat. No. 7,238,022 (Lluch) and U.S. Pat. No. 7,985,070 (Carriere Lluch). This appliance has two segments, with an anterior segment bonded to an anterior tooth (e.g., a cuspid) and a posterior segment bonded to a molar. The anterior segment has an elongated arm that extends posteriorly to seat in a ball-and-socket arrangement with the posterior segment. Each individual Carriere appliance allows only a fixed spacing between the teeth. This fixed length dictates that the orthodontist must maintain an inventory of appliances of different sizes and intradental lengths.

Solution to the Problem

The present invention addresses these shortcomings of the Carriere appliance and other similar appliances by providing a distalizing appliance having an elongated member removably attached between a posterior post bonded to a molar and an anterior button bonded to an anterior tooth. One end of the elongated member is equipped with an eye looped around the posterior post, and the tip at the other end is removably seated in a recess in the anterior button. This allows the tip to be cut to any desired length to accommodate any required spacing between the anterior and posterior teeth.

This "one size fits all" approach dramatically reduces inventory requirements for the orthodontist and reduces manufacturing costs. The present invention also has the advantage of being easy to fabricate in the patient's mouth, if desired, without the need to take impressions or send to a lab.

In addition, the eye of the elongated member allows the elongated member to freely rotate about the posterior post to facilitate easy installation and removal of the elongated arm in the office.

The anterior segment of the present invention is able to move in all three planes due to the two areas of articulation provided at both ends of the elongated member. While the segment is connected and anterior-posterior movement of the bonded teeth is fixed, both the anterior and posterior bonded teeth may move separately in all three planes. In contrast, the Carriere appliance allows only one point of articulation, at the ball joint.

The present appliance provides great versatility in changing the degree of resistance or increasing anchorage by bonding additional teeth along the elongated member, if desired.

SUMMARY OF THE INVENTION

This invention provides an orthodontic appliance having a post attached to a first upper tooth, and a button with a recess attached to a second upper tooth. An elongated arm has an eye at one end through which the post is inserted to allow the elongated arm to rotate about the post, and a tip at the other end for removable insertion into the recess of the button. The length of the elongated arm is selectable to maintain a desired spacing between the first and second upper teeth (e.g., by cutting the tip of the elongated arm). An elastic extends from either the post or button to an attachment point on the patient's lower dental arch to exert a force between the patient's maxilla and mandible. For Class II correction, the elastic biases the mandible forward with respect to the maxilla. For Class III correction, the elastic biases the mandible posteriorly with respect to the maxilla.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 2 is a front view of the posterior post 30.

FIG. 3 is a top view of the posterior post 30.

FIG. 4 is a side view of the posterior post 30.

FIG. 5 is a side view of the anterior button 40.

FIG. 6 is a front view of the anterior button 40.

FIG. 7 is a top view of the anterior button 40.

FIG. 8 is a side view of the elongated arm 20 prior to installation.

DETAILED DESCRIPTION OF THE INVENTION

Figure 1:
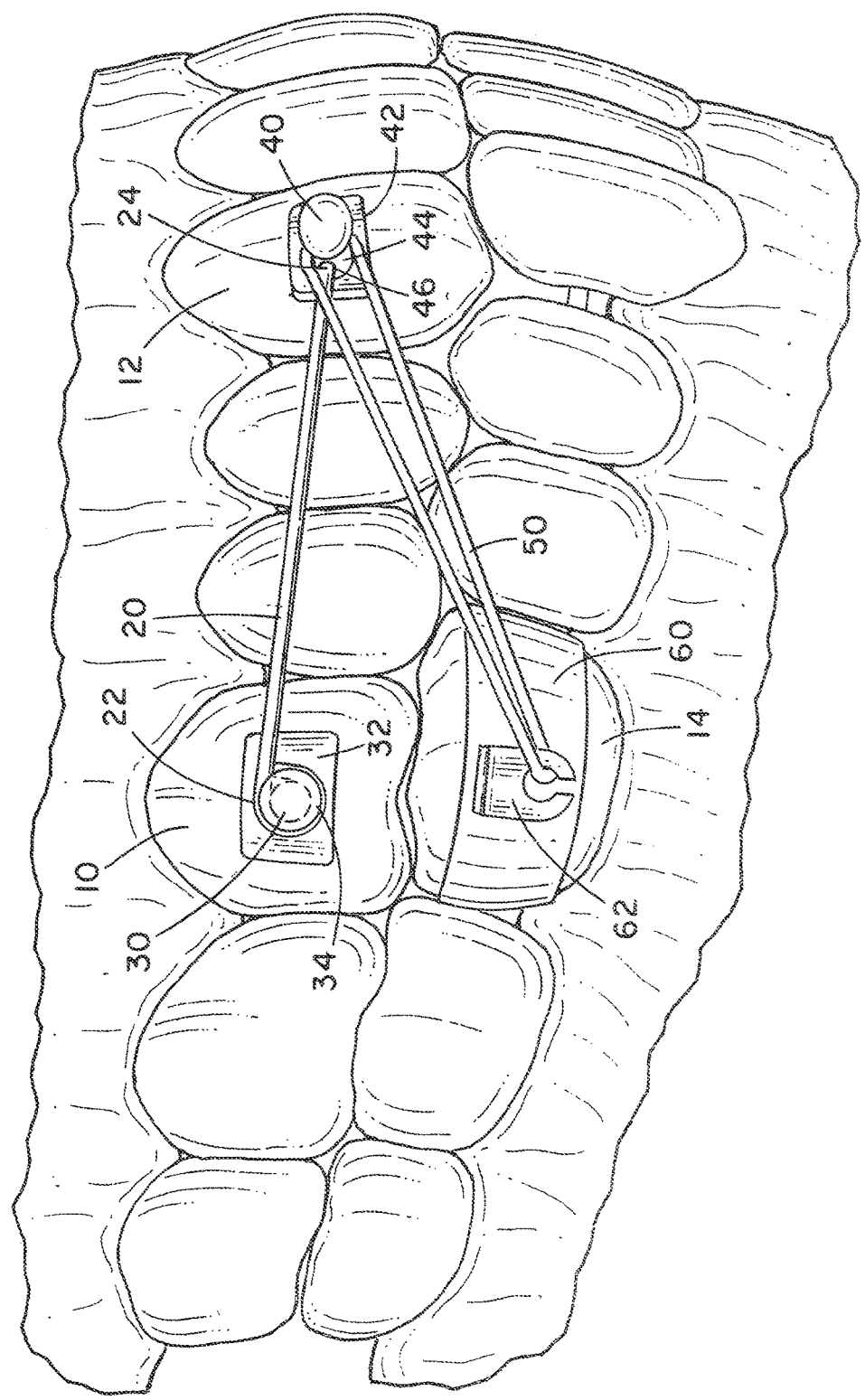
FIG. 1 is a side view of an embodiment of the present invention on a patient's teeth for class II correction.

Turning to FIG. 1, a side view is illustrated of an embodiment of the present invention on a patient's teeth for class II correction. The major components of this orthodontic appliance include a posterior post 30 attached to a upper posterior tooth 10, an anterior button 40 attached to an upper anterior tooth 12, an elongated member 20 extending between the anterior button 40 and the posterior post 30, an elastic 50, and a lower attachment point 62 for the elastic 50, as will be described in greater detail below.

The posterior post 30 has a base 32 suitable for bonding in a conventional manner to a molar 10. The post 30 itself is substantially cylindrical with an enlarged cap 34 at its distal end. Front, top and side views of the posterior post 30 are shown in FIGS. 2-4, respectively.

Similarly, the anterior button 40 has a base 42 suitable for bonding to an anterior tooth 12, such as a cuspid. The button 40 also has a substantially cylindrical shaft 44 with an enlarged head at its distal end for removably engaging an elastic 50, as shown in FIG. 1. A recess or hole 46 in the posterior aspect of the shaft 44 of the button 40 is designed to receive the anterior tip 24 of the elongated member 20, as will be discussed below. FIGS. 5-7 show side, front and top views of the anterior button 40, respectively. Alternatively, the anterior button 40 could have the same overall shape as the posterior post 30 (but with the addition of a recess 46) to simplify manufacturing and reduce costs.

FIG. 8 is a side view of the elongated member 20 prior to installation. For example, the elongated member 20 can be a length of metal wire with a tip 24 at its anterior end, and a loop or crook 22 at its posterior end that wraps around the shaft of the posterior post 30 to form an eye. The enlarged head 34 on the end of the post 30 retains the eye of the elongated arm 20 on the post 30 and allows rotation of the elongated arm 20 about the post 30. Preferably, the post 30 extends horizontally forward from the molar 10 and allows rotation of the elongated arm 20 only in a substantially vertical plane tangential to the upper anterior and posterior teeth 12 and 10.

Figure 11:
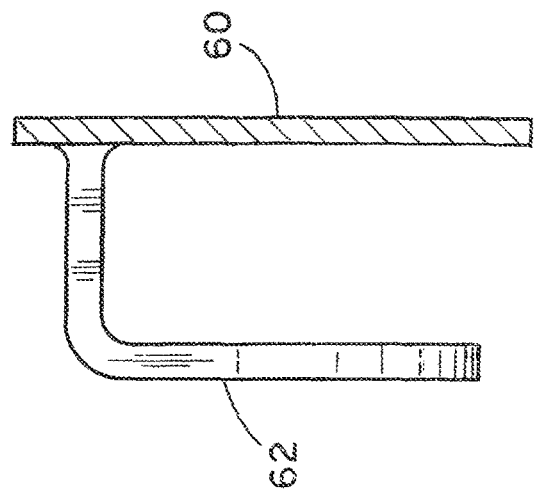
FIG. 11 is a side view of the attachment arm 62 and band 60 corresponding to FIGS. 9 and 10.
Figure 10:
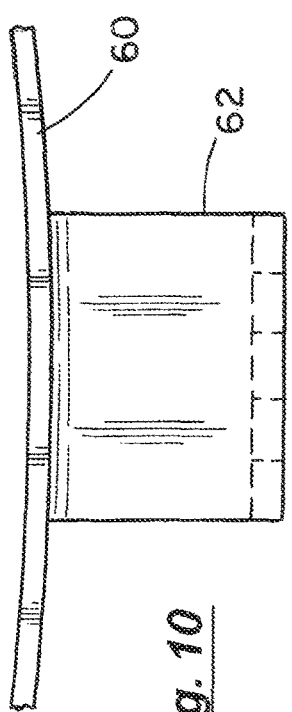
FIG. 10 is a top view of the attachment arm 62 and band 60 corresponding to FIG. 9.
Figure 9:
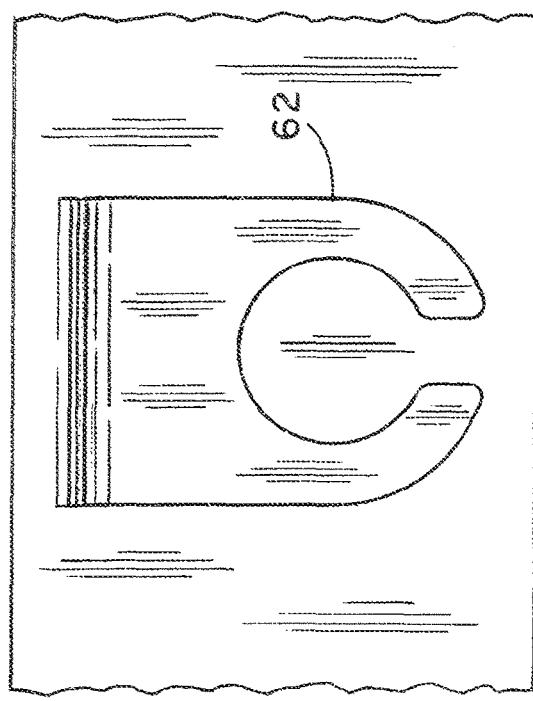
FIG. 9 is a front view of the attachment arm 62 and a portion of the orthodontic band 60 used to secure the lower end of an elastic to a lower molar 14.

FIG. 9 is a front view of the attachment arm 62 and a portion of the orthodontic band 60 used to secure the lower end of an elastic 50 to a lower molar 14. FIGS. 10 and 11 are corresponding top and side views of the attachment arm 62 and orthodontic band 60. A conventional orthodontic band 60 is bonded to a lower molar 14 to support a lower attachment point for the elastic 50 in the embodiment shown the accompanying drawings. Alternatively, a button bonded on a molar or other posterior tooth, or a fixed or removable orthodontic appliance attached to the patient's lower dental arch could be employed as a lower attachment point or additional anchorage for the elastic 50. However, it should be understood that other types of attachment points could be readily substituted. It is also important to prevent undesired movement of the lower molars in response to the forces exerted by the elastics 50. This can be minimized, for example, by means of a mandibular transpalatal arch, lingual holding arch, or overlay retainer.

Returning to FIG. 1, an elastic 50 is stretched between the anterior button 40 on the upper anterior tooth (e.g., cuspid) 12 and the lower attachment arm 62 on the lower posterior tooth (e.g., lower first molar) 14. The resulting force vector biases the mandible forward with respect to the maxilla. The present appliance is primarily intended to be used with elastics 50 that are placed and replaced by the patient. However, a spring (e.g., a DynaFlex CS-2000 spring) may be attached to this appliance in lieu of elastics for forgetful or noncompliant patients.

The following is a discussion concerning installation and use of the present orthodontic appliance. To cause a dentoalveolar effect bringing the lower jaw and teeth forward for class II correction, at least two teeth 10, 12 are attached to the appliance using normal orthodontic bonding techniques. In the specific embodiment shown in FIG. 1, the base 42 of the anterior button 40 is bonded to the upper cuspid 12, and the base 32 of the posterior post 30 is bonded to the upper first molar 10.

During installation, the posterior segment for the molar/posterior tooth 10 with the elongated arm 20 is looped around the shaft of the posterior post 30 to form an eye encircling the posterior post 30, and with the remainder of the wire 20 extending forward. Alternatively, this step can be done during manufacturing, so that the elongated arm 20 comes already connected to the posterior post 30 to the end user. The base 32 of the posterior post 30 is then bonded in place to an upper posterior tooth 10. Next, the tip 24 of the elongated arm 20 is cut to size and slid into the recess 46 on the distal aspect of the anterior button 40. The base 42 of the anterior button 40 is then bonded onto the anterior tooth 12. A lower attachment arm 62 is secured to a lower posterior tooth 14, as discussed above. Finally, the appliance is attached with an elastic 50 extending between the anterior post 40 and the lower attachment arm 62.

The present invention can be employed in an initial phase of treatment for Class II correction prior to conventional orthodontic braces or Invisalign® treatment. Less time may be spent in braces by correcting the patient's teeth to a class I condition first. Anterior-posterior positioning can be the most time-consuming part of treatment. Therefore, undertaking anterior-posterior positioning prior to full orthodontic appliances may decrease the chance of decalcification due to difficulties with oral hygiene while wearing full orthodontic appliance. Compliance is often better at an earlier age as well. The present invention can also be used simultaneously while straightening the lower teeth with conventional orthodontic braces or Invisalign® treatment.

The present device may also be used in Class III situations to correct mild discrepancies or overgrowth. In this configuration, an elastic extends forward from the upper posterior tooth to an anterior anchor point on the lower dental arch to exert a biasing force moving the mandible in a posterior direction. Maxillary anchorage can be obtained with a button on the upper molar and an overlay for support or a transpalatal arch, either of which may be attached to the elastic.

The embodiment of the present invention shown in the drawings has the post 30 on the upper posterior tooth 10 and the button 40 on the upper anterior tooth 12. It should be understood that the positions of these components 30, 40 could be reversed, so that the post 30 is on an anterior tooth and the button 40 is on a posterior tooth. The left-right orientation of the elongated member 20 would also be reversed, so that the tip 24 of the elongated member is inserted into the posterior button.

The present appliance could also be used on the patient's lower dental arch, with an anchor point for the elastic 50 on the upper dental arch. In other words, the post 30 could be attached to a lower posterior tooth and the button 40 could be attached to a lower anterior tooth. The elongated arm 20 would be attached between the lower posterior and anterior teeth. The elastic 50 would stretch between the button 40 on a lower cuspid and an upper attachment arm 62 on an upper molar.

The present invention offers a number of benefits. The present device is a one-size-fits-all appliance, in that the elongated arm 20 is quickly adjusted or clipped to the proper length whereas the Carriere device, by necessity, comes in multiple lengths to fit different length requirements. Because of this, a significant stock of the Carriere device is necessary to have all possible intradental lengths available.

One of the main benefits of the present appliance over using Class II elastics concurrently with braces is the reduced resistance in moving the upper posterior teeth in segments, rather than as an entire dental arch. One of the major factors relating to inter-arch correction to Class I is the amount of bone that directly abuts the tooth surfaces. With the present appliance, as few as two teeth on the upper arch may be in direct opposition to bone. In contrast, when wearing a full set of braces, each tooth connected to the arch wire will increase the amount of bone in opposition to tooth movement, thus increasing the total resistance to tooth movement.

The present appliance is believed to be more hygienic because its components have a smaller footprint vertically, and the round elongated arm 20 is easy to clean.

Vertical force on individual teeth can be controlled by adding or increasing anchorage at any time by bonding additional teeth to the elongated member of the present appliance. This can be done chairside and requires no additional lab time.

The present appliance allows the ability for multi-directional correction simultaneously. For example, this may be accomplished by placing buttons on additional teeth as needed to give the desired force in the desired direction. For another example, the posterior tooth could also be fixed with an elastic starting at the lower first molar, looping over the wire and back down to the lower molar. This facilitates posterior vertical eruption to increase lower face height. This is not possible with the Carriere appliance due to the anterior component being fixed. There is also adequate freedom of movement for the elongated arm 20 in the present appliance to come facially.

As previously noted, the present appliance has two articulation points—at the eye on the wire 20 around the posterior post 30, and the tip 24 of the wire 20 in the recess 46 in the anterior button 40. This enables either or both of the bonded anterior and posterior teeth to move separately, although anterior-posterior movement of the bonded teeth is fixed by the elongated member 20.

The bonded segment in the present invention is able to move in all three planes, as previously noted. This is beneficial because the anterior tooth (e.g., cuspid) is commonly more gingival than desired. In the present appliance, both the anterior and posterior segments can be separately moved. For example, if the orthodontist wishes to allow rotation of the cuspid only, additional teeth near the cuspid may be bonded to the elongated arm 20, thereby effectively fixing the posterior part of the present device into a more resistant section within the segment. However, the cuspid is still free to move or rotate. In essence, the orthodontist is better able to control resistance, or increase anchorage in the anterior or posterior part of the present device by bonding additional teeth.

As another example, the present appliance can be used to allow the anterior tooth to rotate the crown distal to upright, and thereby improve the angle of eruption. This may be stopped at any time. In contrast, the anterior component of the Carriere appliance is fixed. The anterior tooth may also be allowed to rotate distal in (i.e., the distal part of the tooth can be rotated in a palatal direction) by not fully engaging the tip 24 of the elongated member 20 into the recess 46 in the anterior button 40 at the time of bonding. Mild tipping bends may also be placed in the present appliance during treatment to alter the root or tooth position while the appliance is bonded to the teeth. This is not possible with currently available appliances in the market.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. A method of orthodontic treatment of a patient having an upper dental arch and a lower dental arch with a plurality of teeth, said method comprising:

attaching a post to a first tooth in a first of the dental arches;

attaching a button to a second tooth in the first dental arch, said button having a recess extending partially into the button;

providing an elongated arm with a selected length between opposing first and second ends, said elongated arm having:

(a) an eye at the first end through which the post is inserted to allow the elongated arm to rotate about the post, thereby providing articulation at the first end of the elongated arm; and (b) a tip at the second end;

inserting the tip at the second end of the elongated arm into the recess of the button to maintain a fixed spacing between the first and second teeth; and extending an elastic from at least one of the post and button to the patient's other dental arch to exert a force between the patient's maxilla and mandible to bias the mandible in a desired direction with respect to the maxilla while maintaining a fixed spacing between the first and second teeth.

2. The method of claim 1 wherein the elongated arm is formed from a piece of wire having a loop at the first end to form the eye wrapping around the post, and the length of the elongated arm is selected by cutting the second end to a desired length.

3. The method of claim 1 wherein the elastic is secured to a posterior tooth in the patient's other dental arch.

4. The method of claim 1 wherein the elastic is secured to an orthodontic appliance removably attached to the patient's other dental arch.

5. The method of claim 1 wherein the post is attached to an upper posterior tooth and the button is attached to an upper anterior tooth.

6. The method of claim 1 wherein the post further comprises an enlarged head on the end of the post retaining the eye of the elongated arm on the post and allowing rotation of the elongated arm about the post.

7. The method of claim 1 wherein the post extends horizontally from the first tooth and allows rotation of the elongated arm only in a substantially vertical plane tangential to the first and second upper teeth.

8. The method of claim 1 wherein insertion of the tip at the second end of the elongated arm into the recess of the button allows articulation at the second end of the elongated arm with respect to the button.

* * * * *